(12) United States Patent
Döring et al.

(10) Patent No.: US 6,548,700 B2
(45) Date of Patent: Apr. 15, 2003

(54) PROCESS FOR THE PRECIPITATION OF CYSTINE

(75) Inventors: Wolfgang Döring, Burgkirchen (DE); Jürgen Stohrer, Pullach (DE)

(73) Assignee: Consortium fur elektrochemische Industrie GmbH, München (DE)

( * ) Notice: Subject to any disclaimer, the term of this patent is extended or adjusted under 35 U.S.C. 154(b) by 0 days.

(21) Appl. No.: 09/905,359

(22) Filed: Jul. 13, 2001

(65) Prior Publication Data

US 2002/0022744 A1 Feb. 21, 2002

(30) Foreign Application Priority Data

Aug. 17, 2000 (DE) .......................... 100 40 177

(51) Int. Cl.$^7$ ...................... C07C 323/00; C07C 227/00
(52) U.S. Cl. ........................ 562/557; 562/554; 562/556
(58) Field of Search ................................ 562/557, 556, 562/554

(56) References Cited

FOREIGN PATENT DOCUMENTS

| | | |
|---|---|---|
| DE | 907 175 | 3/1954 |
| JP | 60064956 | * 4/1983 |
| WO | 87 05895 | 10/1987 |

OTHER PUBLICATIONS

Pavia et al, Organic laboratory Techniques, Second Edition, Saunders College Publishing, 1995, p. 600.*
Caplus Abstract AN 1958: 56100 corresp, to DE 907 175.

* cited by examiner

Primary Examiner—Johann Richter
Assistant Examiner—Paul A. Zucker

(57) ABSTRACT

A process for precipitating cystine from a solution in sulfuric acid, includes forming a mixture of a solution of cystine in aqueous sulfuric acid and of an aqueous solution of a base by simultaneous metering the cystine solution and the aqueous base solution into a mixing container. The metering takes place in such a way that the mixture in the container has a pH between 1.0 and 7.0 and a temperature between 30° C. and the boiling point of the mixture.

11 Claims, No Drawings

PROCESS FOR THE PRECIPITATION OF CYSTINE

BACKGROUND OF THE INVENTION

1. Field of the Invention

The present invention relates to a process for the precipitation of the amino acid cystine from a solution in sulfuric acid.

2. The Prior Art

The amino acid cystine is usually obtained by acid hydrolysis of keratinous waste products such as, for example, human hair, and is purified by reprecipitation. Reprecipitatibn from solution in hydrochloric acid is well known in this field of technology. Multiple application of reprecipitation allows a crystalline product to be isolated which meets the purity requirements for the target markets (foodstuff specifications such as, for example, FCC IV for USA and drug specifications such as, for example, USP 23 for USA, Ph.Eur.2000 for Europe). This usually entails initially the cystine solution in (hydrochloric) acid being brought to the precipitation temperature, and then the base, usually aqueous ammonia or aqueous sodium hydroxide solution, being metered in until the pH is at a defined value (mostly between 0.6 and 3.5).

Although application of this process to a solution of cystine in sulfuric acid likewise results in very pure cystine, it always comprises a certain residual sulfate content. This is, depending on the experimental conditions, between 400 and 1500 ppm. The maximum residual sulfate permitted required by Ph. Eur. must, however, be only 300 ppm.

SUMMARY OF THE INVENTION

It is an object of the present invention to provide a process which makes it possible to precipitate solid crystals of cystine which has a residual sulfate content of less than 300 ppm, which additionally meets all the other purity criteria of the foodstuff and drug specifications applicable to a solution in sulfuric acid.

The above object is achieved by the present invention which relates to a process for precipitating solid crystals of cystine which comprises forming a mixture of a solution of cystine in aqueous sulfuric acid and of an aqueous solution of a base by simultaneous metering into a mixing container the solution of cystine and the solution of the base; the metering taking place in such a way that the mixture in the container has a pH between 1.0 and 7.0 and a temperature between 30° C. and the boiling point of the mixture; and precipitating solid crystals of cystine.

The concentration of cystine in the added solution is between 20 g/l and 200 g/l, preferably 40 g/l to 180 g/l, particularly preferably 50 to 150 g/l.

The molar excess of sulfuric acid in the added solution based on cystine is chosen to be as small as possible so that the $H_2SO_4$:cystine molar ratio is preferably from 1.5 to 3.0, particularly preferably 2.0 to 2.5.

The aqueous solution of a base is preferably selected from the group consisting of an aqueous ammonia solution, an aqueous solution of an alkali metal hydroxide, an aqueous solution of an alkali metal bicarbonate, an aqueous solution of an alkali metal carbonate or a mixture of these solutions.

An aqueous solution of ammonia, an aqueous solution of sodium hydroxide or an aqueous solution of potassium hydroxide is preferably used.

The concentration of the base can be varied within a wide range and is preferably between 10% and 50% by weight based upon the total weight of the aqueous solution of the base.

The pH is kept constant within a range from 1.0 to 7.0, preferably 1.5 to 5.0, particularly preferably 1.8 to 3.5, during the precipitation by adjusting the metering rates.

The variation between the lowest and highest pH in the mixture during a single precipitation is preferably less than 3 pH units.

The temperature during the precipitation is kept at between 30° C. and the boiling point of the mixture, preferably between 40° C. and the boiling point of the mixture, particularly preferably between 50° C. and the boiling point of the mixture.

Precipitation of the solid crystals of cystine can be carried out both batchwise and continuously.

In a batchwise management of the process, firstly a small amount of water or mother liquor from a preceding precipitation is introduced into the mixing container. After the contents of the mixing container have been brought to the precipitation temperature, the components are then metered in as described. A particularly slow metering generally has beneficial effects on the purity of the product. However for economic reasons, the total duration of the metering is to be chosen preferably between 0.5 and 6 h, particularly preferably between 1 and 3 h.

The components may however be heated individually to the precipitation temperature before being introduced into a mixing container, or be brought to the desired precipitation temperature only when in the mixing container.

In a continuous procedure, the components are individually heated to the precipitation temperature before being introduced into the mixing container, and are then metered into the mixture.

After the precipitation of the solid crystals of cystine has been carried out, the crystals are removed from the mother liquor by a solid/liquid separation such as, for example, centrifugation, filtration or sedimentation of the mixture.

Preferred solid/liquid separations are centrifugation and filtration.

The separation of the solid crystals of cystine from the mother liquor can be carried but as is known for the separation after precipitation from solution in hydrochloric acid. It is an advantage of the process of the invention that no corrosion problems occur as do result with the chloride-containing, acid solutions from the prior art.

The solid crystals of cystine are then washed with water, preferably with deionized water. The amount of water is such that sulfate is no longer detectable in the filtrate which drains off using a 10% strength barium chloride aqueous solution. From 5 to 20 volumes of water based on the dry weight of the crystals are preferably employed. The amount of water is moreover preferably divided into from 3 to 20 portions.

Other objects and features of the present invention will become apparent from the following detailed description considered in connection with the accompanying Examples which disclose several embodiments of the present invention. It should be understood, however, that the Examples are designed for the purpose of illustration only and not as a definition of the limits of the invention.

DETAILED DESCRIPTION OF PREFERRED EMBODIMENTS

EXAMPLE 1

250 ml of $H_2O$ were introduced into a 1 l glass stirred reactor. After heating to 60° C., 340 ml of the cystine solution in sulfuric acid with an L-cystine content of about 100 g/l were metered in with stirring at this temperature over the course of 2 h. At the same time, a 25% by weight aqueous ammonia solution was metered in so that a pH of about 3.0 was maintained. The mixture was then cooled to 20° C., and the precipitated solid was filtered off and washed with a total of 600 ml of $H_2O$. Drying in vacuo at 70° C. resulted in 33.3 g (98%) of L-cystine. The sulfate content of the product was 275 ppm.

EXAMPLE 2

250 ml of $H_2O$ were introduced into a 1 l glass stirred reactor. After heating to 80° C., 400 ml of the cystine solution in sulfuric acid with an L-cystine content of about 93 g/l were metered in with stirring at this temperature over the course of 2 h. At the same time, a 25% by weight aqueous ammonia solution was metered in so that a pH of about 2.3 was maintained. The mixture was then cooled to 20° C., and the precipitated solid was filtered off and washed with a total of 600 ml of $H_2O$. Drying in vacuo at 70° C. resulted in 36.0 g (97%) of L-cystine. The sulfate content of the product was 208 ppm.

EXAMPLE 3

250 ml of $H_2O$ were introduced into a 1 l glass stirred reactor. After heating to 60° C., 360 ml of the cystine solution in sulfuric acid with an L-cystine content of about 100 g/l were metered in with stirring at this temperature over the course of 2 h. At the same time, a 20% by weight aqueous sodium hydroxide solution was metered in so that a pH of about 4.0 was maintained. The mixture was then cooled to 20° C., and the precipitated solid was filtered off and washed with a total of 600 ml of $H_2O$. Drying in vacuo at 70° C. resulted in 34.7 g (97%) of L-cystine. The sulfate content of the product was 170 ppm.

EXAMPLE 4

15 l of water were introduced into a 60 l enamel vessel and heated to 60° C. While stirring at this temperature, 46 l of a cystine solution in sulfuric acid with a L-cystine content of about 82 g/l were metered in over the course of 2 h. At the same time, a 25% by weight aqueous ammonia solution was metered in so that a pH of about 3.0 was maintained. The mixture was then cooled to 20° C., and the precipitated solid was filtered off and washed with 10 portions each of 10 l of $H_2O$. Drying in vacuo at 70° C. resulted in 3.57 kg (95%) of L-cystine. The sulfate content of the product was 290 ppm.

COMPARATIVE EXAMPLE 1

250 ml of $H_2O$ were introduced into a 1 l glass stirred reactor. While stirring at 20° C., 360 ml of a cystine solution in sulfuric acid with an L-cystine content of about 100 g/l were metered in over the course of 2 h. At the same time, a 25% by weight aqueous ammonia solution was metered in so that a pH of about 3.0 was maintained. The precipitated solid was then filtered off and washed with a total of 600 ml of $H_2O$. Drying in vacuo at 70° C. resulted in 35.2 g (98%) of L-cystine. The sulfate content of the product was 580 ppm.

COMPARATIVE EXAMPLE 2

74 l of a cystine solution in sulfuric acid with an L-cystine content of about 104 g/l were introduced into a 100 l enamel vessel and heated to 60° C. Then 7.0 kg of a 25% by weight aqueous ammonia solution were added at this temperature over the course of 40 min. The pH after the addition was 3.0. Cooling to 20° C. was followed by filtration, washing with 12 portions each of 10 l $H_2O$ and drying in vacuo at 70° C. 7.43 kg (97%) of L-cystine were obtained. The sulfate content of the product was 800 ppm.

Accordingly, while a few embodiments of the present invention have been shown and described, it is to be understood that many changes and modifications may be made thereunto without departing from the spirit and scope of the invention as defined in the appended claims.

What is claimed is:

1. A process for precipitating solid cystine crystals from a solution in sulfuric acid, which comprises
    forming a mixture of a solution of cystine in aqueous sulfuric acid and of an aqueous solution of a base by simultaneous metering said cystine solution and said aqueous solution of a base into a mixing container;
    the metering taking place in such a way that the mixture in the container has a pH between 1.0 and 7.0 and a temperature between 30° C. and the boiling point of the mixture; and
    precipitating solid crystals of cystine, which have a residual sulfate content of less than 300 ppm.

2. The process as claimed in claim 1,
    wherein cystine concentration in the aqueous sulfuric acid is between 20 and 200 g/l.

3. The process as claimed in claim 1,
    wherein the solution of cystine in aqueous sulfuric acid has an $H_2SO_4$:cystine molar ratio of from 1.5 to 3.0.

4. The process as claimed in claim 1,
    wherein the aqueous solution of a base is selected from the group consisting of an aqueous ammonia solution, an aqueous solution of an alkali metal hydroxide, an aqueous solution of an alkali metal bicarbonate, an aqueous solution of an alkali metal carbonate, and a mixture of these solutions.

5. The process as claimed in claim 4,
    wherein the aqueous solution of a base is selected from the group consisting of an aqueous solution of ammonia, and an aqueous solution of potassium hydroxide, and an aqueous solution of sodium hydroxide.

6. The process as claimed in claim 1,
    wherein the concentration of the base is between 10% and 50% by weight, based upon the total weight of the aqueous solution of the base.

7. The process as claimed in claim 1,
    wherein the variation between the lowest and highest pH in the mixture during a precipitation is preferably less than 3 pH units.

8. The process as claimed in claim 1, comprising removing solid crystals of cystine by a solid/liquid separation after precipitation.

9. The process as claimed in claim 8, comprising using filtration or centrifugation as the solid/liquid separation.

10. The process as claimed in claim 8, comprising washing the solid crystals cystine with water, with the amount of water being such that sulfate is no longer detectable in the filtrate which drains off using a 10% strength barium chloride aqueous solution.

11. The process as claimed in claim 1,
    wherein precipitation of the solid crystals of cystine is selected from the group consisting of batchwise and continuously.

* * * * *